US012746375B2

(12) United States Patent
Hara et al.

(10) Patent No.: US 12,746,375 B2
(45) Date of Patent: Sep. 29, 2026

(54) PRESSURIZING DEVICE

(71) Applicant: GOODMAN CO., LTD., Nagoya (JP)

(72) Inventors: Daiki Hara, Seto (JP); Masahiko Ota, Seto (JP)

(73) Assignee: GOODMAN CO., LTD., Nagoya (JP)

( * ) Notice: Subject to any disclaimer, the term of this patent is extended or adjusted under 35 U.S.C. 154(b) by 779 days.

(21) Appl. No.: 18/154,264

(22) Filed: Jan. 13, 2023

(65) Prior Publication Data

US 2023/0166089 A1 Jun. 1, 2023

Related U.S. Application Data

(63) Continuation of application No. PCT/JP2021/023615, filed on Jun. 22, 2021.

(30) Foreign Application Priority Data

Jul. 15, 2020 (JP) ................................ 2020-121271

(51) Int. Cl.
*A61M 25/10* (2013.01)

(52) U.S. Cl.
CPC ............................ *A61M 25/10182* (2013.11); *A61M 25/10187* (2013.11); *A61M 25/104* (2013.01)

(58) Field of Classification Search
CPC ........ A61M 25/1018; A61M 25/10182; A61M 25/10187; A61M 25/104;

(Continued)

(56) References Cited

U.S. PATENT DOCUMENTS 2,221,739 A 11/1940 Reiter
4,832,692 A * 5/1989 Box ................ A61M 25/10182 604/920

(Continued)

FOREIGN PATENT DOCUMENTS

| | | | |
|---|---|---|---|
| CN | 101732791 | A | 6/2010 |
| EP | 1400213 | A1 | 3/2004 |
| JP | 2004-525696 | A | 8/2004 |

OTHER PUBLICATIONS

Oct. 24, 2023—(JP) Notice of Reasons for Refusal—JP App 2022-536205, Eng Tran.

(Continued)

*Primary Examiner* — Chelsea E Stinson
*Assistant Examiner* — Hamza A Darb
(74) *Attorney, Agent, or Firm* — Banner & Witcoff, Ltd.

(57) ABSTRACT

The pressurizing device includes a syringe configured to store a fluid, a plunger for discharging the fluid to the outside of the syringe when the plunger moves to one side in a first direction, a regulating member configured to move in a second direction intersecting the first direction, between a separated position of being separated from the plunger and a contact position of being in contact with the plunger, a lever configured to move the regulating member from the contact position to the separated position, and a rotation mechanism provided at a position overlapping with the regulating member in the second direction, configured to move in the second direction in accordance with rotation of the lever, and configured to move, when moving to one side in the second direction, the regulating member from the contact position to the separated position.

7 Claims, 13 Drawing Sheets

(58) Field of Classification Search
CPC ...... A61M 25/10184; A61M 25/10188; A61M 25/1085; A61M 2005/3139; A61M 5/1456
See application file for complete search history.

(56) References Cited

U.S. PATENT DOCUMENTS

| | | | | |
|---|---|---|---|---|
| 4,940,459 | A | 7/1990 | Noce | |
| 6,106,496 | A * | 8/2000 | Arnissolle ....... | A61M 25/10182 604/207 |
| 2002/0133116 | A1* | 9/2002 | Davis .................. | A61M 25/104 604/97.01 |
| 2004/0255448 | A1 | 12/2004 | Davis et al. | |
| 2009/0227947 | A1* | 9/2009 | Caclin ............. | A61M 25/10182 604/97.02 |
| 2010/0116360 | A1 | 5/2010 | Kanner et al. | |

OTHER PUBLICATIONS

Jan. 17, 2023—(WO) International Preliminary Reprot on Patentability—Intl App PCT/JP2021/023615, Eng Tran.
Mar. 31, 2023—(CN) First Office Action—CN App 202180016342.0, Eng Tran.
Sep. 7, 2021—International Search Report—Intl App PCT/JP2021/023615.
Sep. 2, 2025—(ID) Office Action—Indonesian App P00202301105, Eng Tran.
Jan. 21, 2026—(IN) First Examination Report—App 202317004471.

* cited by examiner

PRESSURIZING DEVICE

REFERENCE TO RELATED APPLICATIONS

This application is a Continuation Application of International Application No. PCT/JP2021/023615, filed Jun. 22, 2021, which claims priority from Japanese Patent Application No. 2020-121271, filed on Jul. 15, 2020. This disclosure of the foregoing application is hereby incorporated by reference in its entirety.

BACKGROUND ART

In the medical field, a technique is known for treating a constriction in a living organism using a dilator, such as a balloon or the like. Further, as a device for inflating the dilator, a pressurizing device is known that pressure feeds a pressurizing medium formed from a fluid or the like to the dilator.

A pressurizing device provided with a housing, a plunger, a nut member, a knob, and the like is known. A hose is connected to the housing. A piston, which includes a space communicated with the hose, is provided inside the housing. The plunger and the nut member are respectively provided with screw portions. As a result of the knob being rotated in a state in which the screw portion of the nut member is engaged with the screw portion of the plunger, the plunger moves inside the housing in a direction approaching the hose. At this time, a fluid inside the space of the piston flows out toward the hose. When a balloon is connected to the hose, for example, the balloon is inflated by the fluid that has flowed out to the hose. On the other hand, the nut member is displaced by operation of a handle. The engaged state of the screw portion of the plunger with respect to the screw portion of the nut member is released. At this time, the plunger moves inside the housing in a direction separating from the hose. When the balloon is in an inflated state, for example, the fluid is discharged from the balloon, and the balloon rapidly deflates.

DESCRIPTION

There is a case in which a lever is used as a mechanism for releasing an engaged state of a screw portion of a plunger with respect to a screw portion of a nut member. The lever applies a force to the nut member as a result of rotating, and separates the screw portion of the plunger from the screw portion of the nut member. For example, when a balloon is in an inflated state due to a fluid, an urging force acts on the plunger, and it is thus difficult for the screw portion of the plunger to be separated from the screw portion of the nut member. Thus, when the engaged state is released by a user operating the lever, it is necessary to operate the lever using a large amount of force, and there is a problem that operability deteriorates.

An object of the present disclosure is to provide a pressurizing device that is easy to operate.

A pressurizing device of the present disclosure includes a syringe, a plunger, a regulating member, a lever, and a rotation mechanism. The syringe internally includes a storage portion configured to store a fluid. The plunger is configured to move in a first direction with respect to the syringe, and discharging the fluid stored in the storage portion to the outside of the syringe when the plunger moves to one side in the first direction. The regulating member is configured to move in a second direction intersecting the first direction, between a separated position of being separated from the plunger and a contact position of being in contact with the plunger. The lever is configured to move the regulating member from the contact position to the separated position in accordance with a rotation operation. The rotation mechanism is provided at a position overlapping with the regulating member in the second direction, The rotation mechanism supports the lever to be rotatable with respect to the regulating member. The rotation mechanism is configured to move in the second direction in accordance with rotation of the lever. The rotation mechanism is configured to move, when moving to one side in the second direction, the regulating member from the contact position to the separated position by applying a force to the regulating member.

When the lever is operated and rotated, the lever can apply a force oriented toward the one side in the second direction to the regulating member, and can move the regulating member from the contact position to the separated position. In this case, a force required to operate the lever in order to move the regulating member from the contact position to the separated position is small, compared to when the force applied to the regulating member by the lever is diffused in a direction other than the one side in the second direction. Thus, the pressurizing device can improve operability for a user.

Further, a housing of the pressurizing device disclosed in Patent Literature 1 may be formed by combining a syringe with a body including a nut portion and the like. Here, a significant pressure is applied inside the housing when using the pressurizing device. Thus, a mechanism that firmly couples the syringe and the housing is required.

Another object of the present disclosure is to provide a pressurizing device capable of firmly coupling a syringe and a body.

A pressurizing device according to another aspect of the present disclosure includes: a syringe internally including a storage portion configured to store a fluid; a plunger configured to move in a first direction with respect to the syringe, and discharging the fluid stored in the storage portion to the outside of the syringe when the plunger moves to one side in the first direction; a regulating member configured to regulate movement of the plunger; a body disposed on another side in the first direction with respect to the syringe, and configured to support the regulating member; and a coupling mechanism configured to couple the syringe and the body. The coupling mechanism includes: a base portion provided on one of the syringe and the body, and extending toward the other of the syringe and the body along the first direction; an elastic portion being part of the base portion, and extending from a proximal end toward a distal end along a rotational direction centered on a center line extending in the first direction along the plunger; a first protruding portion provided on a part including the distal end of the elastic portion, protruding in a radial direction with respect to the center line as a reference, and having a height in the radial direction that gradually increases from the proximal end toward the distal end; and an engagement portion provided on the other of the syringe and the body, and configured to engage with the first protruding portion. The coupling mechanism couples the syringe and the body as a result of the syringe and the body being rotated relative to each other in the rotational direction in a state of the engagement portion being disposed to the same side as the proximal end with respect to the first protruding portion, and the engagement portion moving to an opposite side from the proximal end with respect to the first protruding portion.

When the syringe and the body are coupled together, the first protruding portion moves in accordance with an elastic force of the elastic portion, and the first protruding portion and the engagement portion engage with each other. As a result, the pressurizing device can strongly couple the syringe and the body using the coupling mechanism without using an adhesive or the like, and thus, can reduce the possibility of the adhesive or the like becoming mixed in with a fluid. Further, a direction of relative movement of the syringe and the body with respect to each other in a process to couple the syringe and the body (the rotational direction) is orthogonal to an arrangement direction of the syringe and the body (the first direction). Thus, even if a force acts on the syringe and the body in the first direction to cause the syringe and the body to separate from each other, the pressurizing device can effectively suppress the syringe and the body from becoming detached from each other. As a result, the pressurizing device can maintain a state in which the syringe and the body are firmly coupled to each other for a long period of time.

According to another aspect, a first end portion on a side closer to the engagement portion, of the first protruding portion, and a second end portion closer to the first protruding portion, of the engagement portion, respectively include flat surfaces extending along the radial direction, and rotation of the syringe and the body relative to each other is regulated by the first end portion and the second end portion coming into contact with each other.

In this case, the first end portion and the second end portion come into contact with each other over a wide area of the flat surfaces, and regulate the rotation of the body with respect to the syringe. Thus, the pressurizing device can maintain the coupled state of the syringe and the body in a stable manner, and can suppress occurrence of dimensional error between each of units.

According to another aspect, the coupling mechanism includes: a second protruding portion protruding in the radial direction from the base portion, and including a protrusion at an end portion on an opposite side from the base portion; and a groove portion, provided on the other of the syringe and the body, into which the second protruding portion fits.

In this case, even if slight irregularities are formed on a bottom portion of the groove portion, a distal end portion of the second protruding portion, or the like, the protrusion can stabilize a position, in the radial direction, of the second protruding portion in the groove portion. Thus, using the protrusion, the pressurizing device can resolve dimensional errors of the syringe and the body.

A pressurizing device 1 that is an embodiment of the present disclosure will be described. In the following description, an upper side, a lower side, a left upper side, a right lower side, a left lower side, and a right upper side are respectively defined as an upper side, a lower side, a left side, a right side, a distal end side, and a proximal end side of the pressurizing device 1. A direction extending between the distal end side and the proximal end side is defined as an extending direction.

Overview of Pressurizing Device 1

Figure 1:
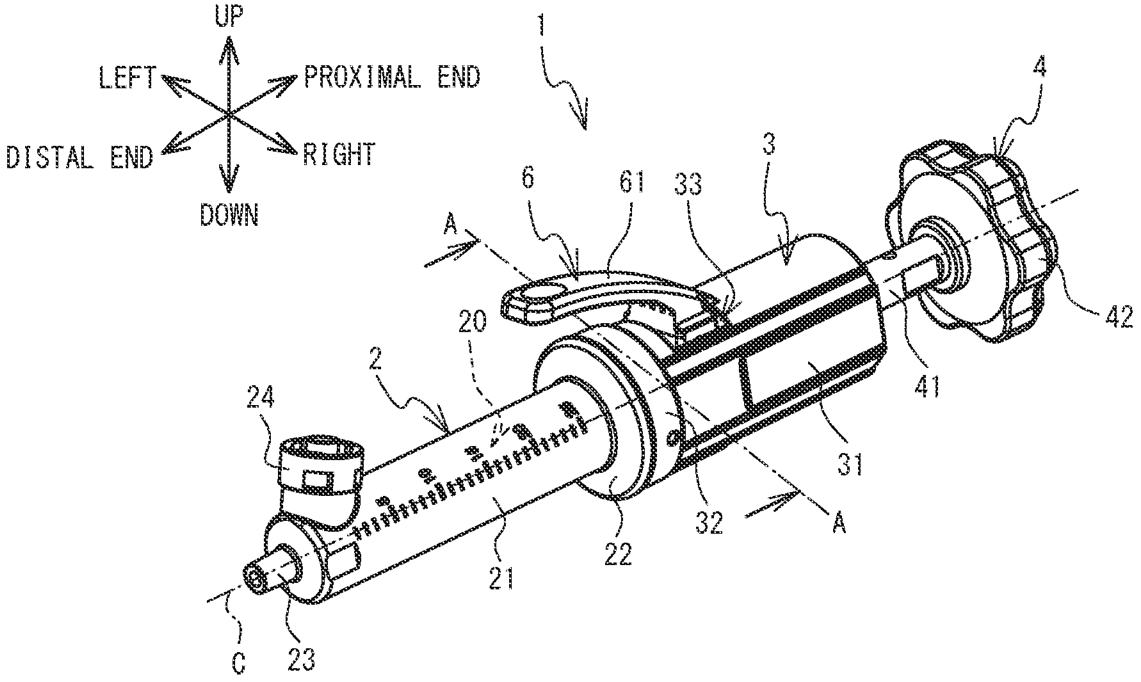
FIG. 1 is a perspective view of a pressurizing device.
Figure 2:
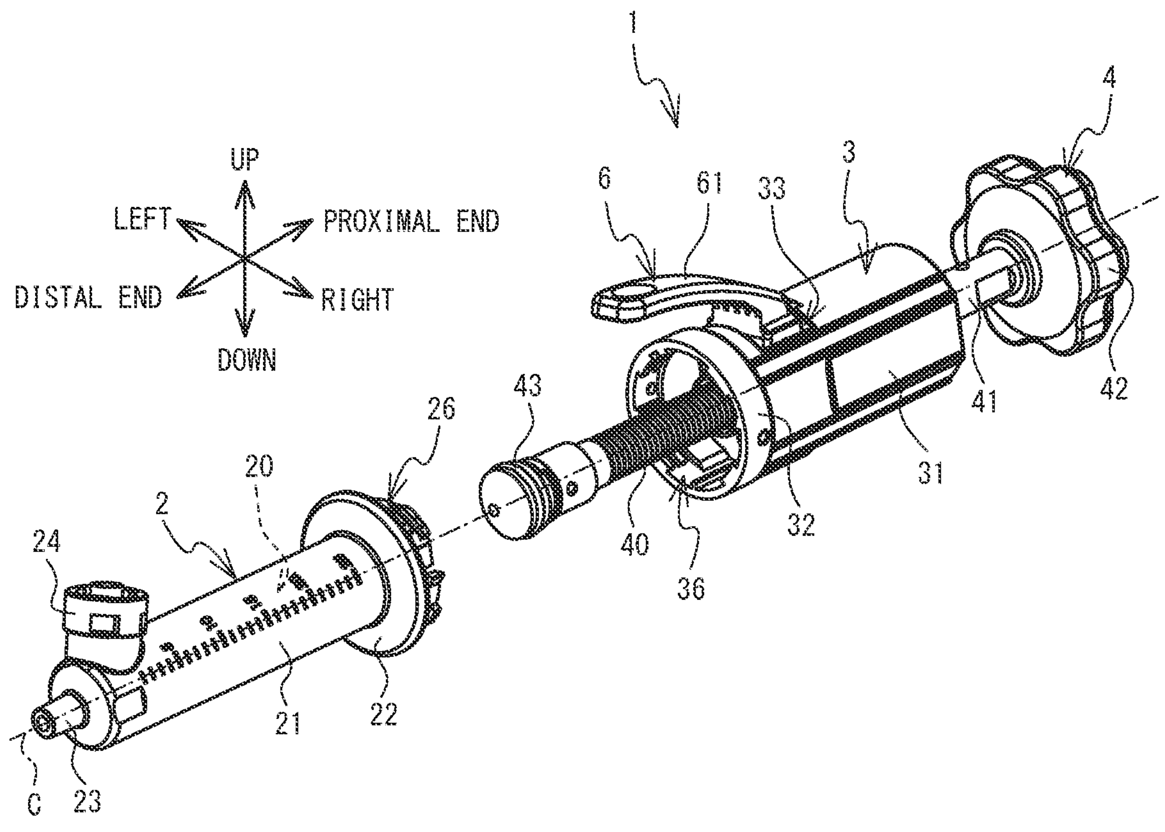
FIG. 2 is an exploded perspective view of the pressurizing device.
Figure 3:
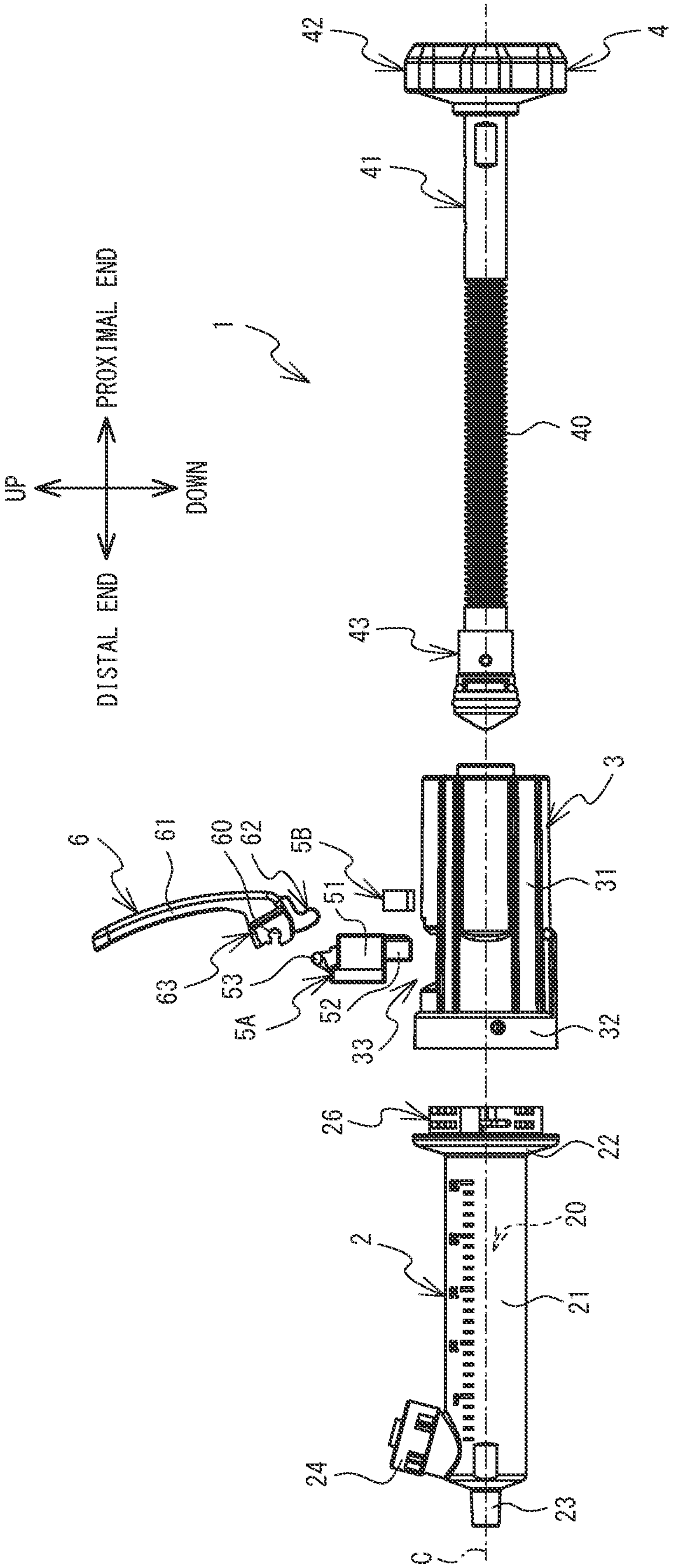
FIG. 3 is an exploded side view of the pressurizing device.

The pressurizing device 1 is an indeflator, for example, and can be used for deforming (inflating or deflating) a balloon (not shown in the drawings) used for expanding a constriction. As shown in FIG. 1 to FIG. 3, the pressurizing device 1 is provided with a syringe 2, a body 3, a plunger 4, a regulating body 5A (refer to FIG. 3), an urging member 5B (refer to FIG. 3), and a lever body 6. The pressurizing device 1 pressure feeds a fluid housed in the syringe 2 to the inside of the balloon via a catheter, and inflates the balloon. The plunger 4 is operated when pressure feeding the fluid from the syringe 2. Further, the pressurizing device 1 can discharge the fluid from inside the balloon in accordance with an operation of the lever body 6 supported by the body 3, and can cause the balloon to deflate.

Syringe 2

The syringe 2 includes a cylindrical body 21, a flange 22, a connection port 23, a pressure gage connection port 24, and a coupling portion 26 (refer to FIG. 2 and FIG. 3). The cylindrical body 21 is a transparent member having a cylindrical shape. A proximal end of the cylindrical body 21 is open. The cylindrical body 21 internally includes a storage portion 20 that can store the fluid. A virtual line extending in the extending direction and passing through the center of the cylindrical body 21 will be referred to as a center line C. A scale for verifying a volume of the fluid stored in the storage portion 20 is provided in a side surface of the cylindrical body 21.

The flange 22 is provided at the proximal end portion of the cylindrical body 21, and protrudes outward. As shown in FIG. 2 and FIG. 3, the coupling portion 26 for coupling the syringe 2 and the body 3 is provided at a surface on the proximal end side of the flange 22. The coupling portion 26 will be described in detail later. As shown in FIG. 1 to FIG. 3, the connection port 23 is provided at a distal end portion of the cylindrical body 21. The connection port 23 has a cylindrical shape having a smaller diameter than that of the cylindrical body 21. The connection port 23 extends from the distal end portion of the cylindrical body 21 toward the distal end side, along the center line C. One end of a resin tube (not shown in the drawings) is connected to the connection port 23. A three-way cock is connected to the other end of the resin tube, and a catheter (not shown in the drawings) that is coupled to the balloon is coupled to the distal end of the three-way cock. The pressure gage connection port 24 is provided in the vicinity of the distal end portion, of the side surface of the cylindrical body 21. A pressure gage (not shown in the drawings) for measuring the pressure of the fluid stored inside the storage portion 20 is connected to the pressure gage connection port 24.

Coupling Portion 26

Figure 4:
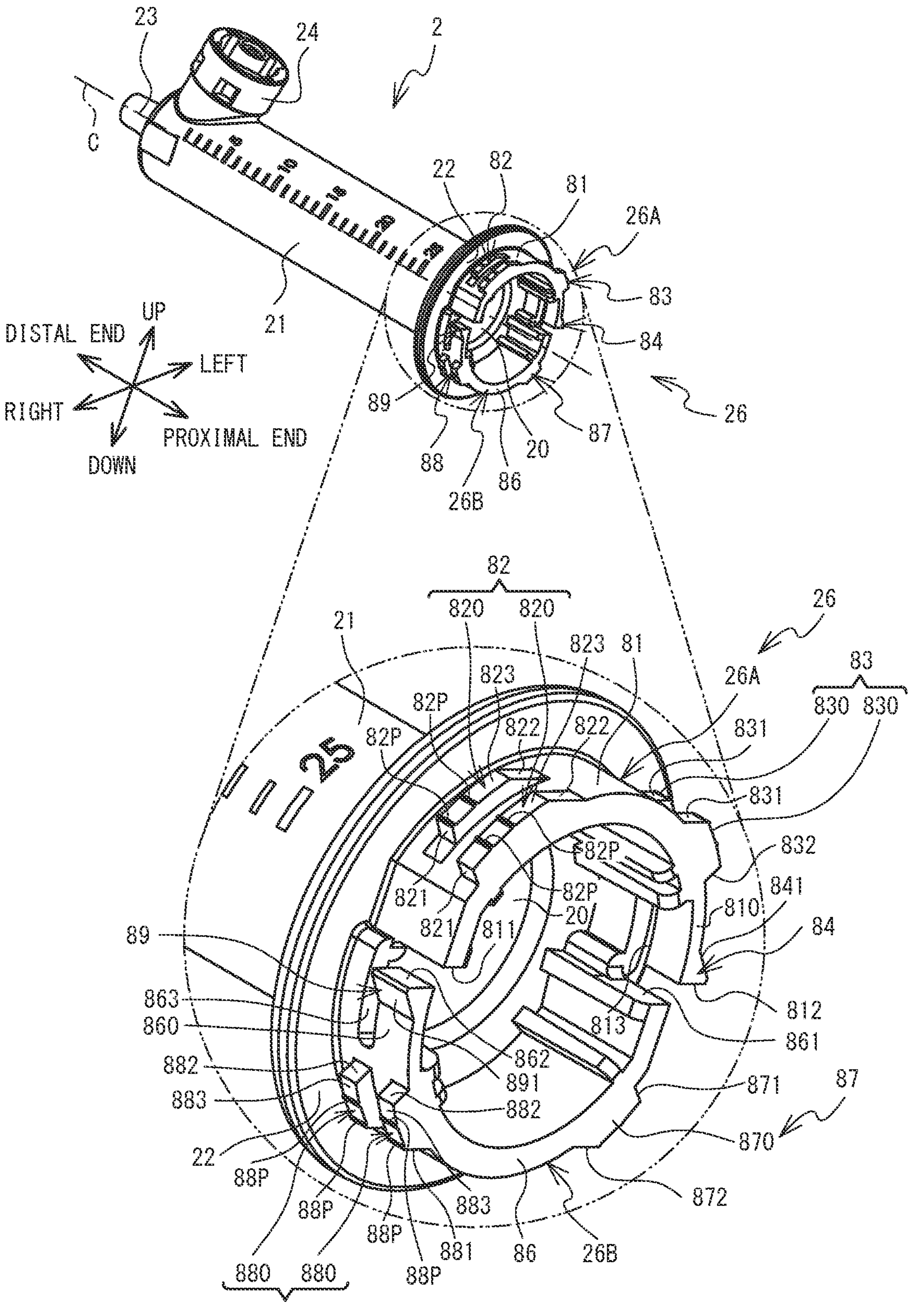
FIG. 4 is an expanded perspective view of a syringe.

As shown in FIG. 4, the coupling portion 26 includes coupling bodies 26A and 26B. The shapes of the coupling bodies 26A and 26B have a point symmetrical relationship, with the center line C being a rotational center. The coupling body 26A includes a base portion 81, and protruding portions 82, 83, and 84. The coupling body 26B includes a base portion 86, and protruding portions 87, 88, and 89. Hereinafter, insofar as there is no particular description, a state in which the coupling portion 26 is seen from the distal end side (a state shown in FIG. 6 and FIG. 7) defines a rotational direction centered on the center line C (a clockwise direction and a counter-clockwise direction). Further, the coupling body 26A will be described in detail and a description of the coupling body 26B will be simplified.

Figure 6:
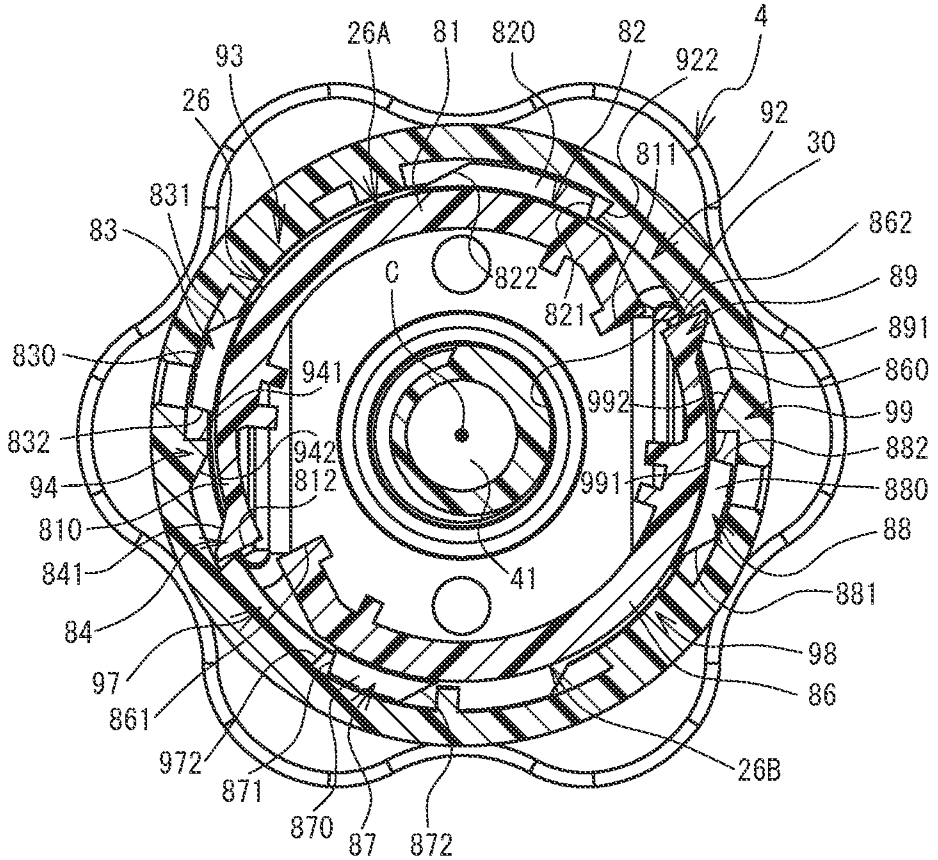
FIG. 6 is a cross-sectional view (before coupling), as seen from the direction of arrows, of a line A-A shown in FIG. 1.
Figure 7:
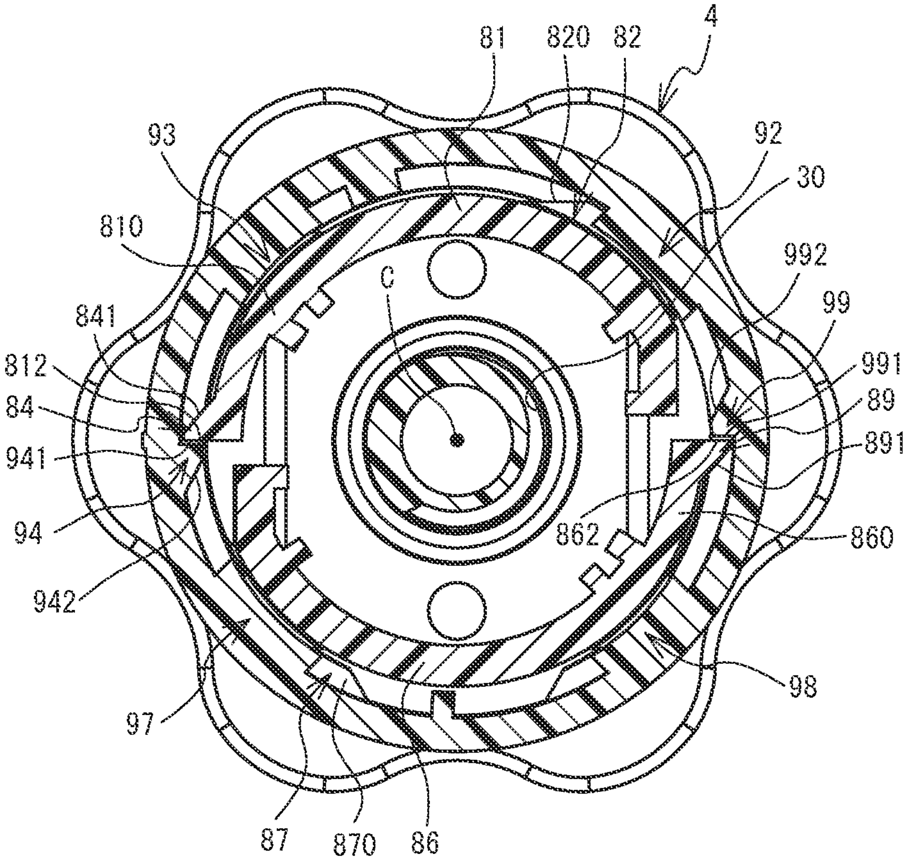
FIG. 7 is a cross-sectional view (after coupling), as seen from the direction of the arrows, of the line A-A shown in FIG. 1.

The base portion 81 has a curved plate shape, and extends from the surface at the proximal end side of the flange 22 of the syringe 2 toward the proximal end side. The base portion 81 has a circular arc shape centered on the center line C, when seen from the proximal end side. The shape of the base portion 81 corresponds to an upper side portion of respective portions obtained by dividing, in the up-down direction, a circular cylindrical body that extends in the extending direction along the center line C. The base portion 81 curves so as to have an upward convex shape. End portions at both ends in the circumferential direction of the base portion 81 will be referred to as end portions 811 and 812. As shown in FIG. 6 and FIG. 7, a direction along the base portion 81 from the end portion 811 toward the end portion 812 is the counter-clockwise direction. The protruding portions 82, 83, and 84 are provided on the outer side surface of the base portion 81. The protruding portions 82, 83, and 84 are aligned in that order in the counter-clockwise direction. The protruding portion 84 is provided at the end portion 812 of the base portion 81.

As shown in FIG. 4, the protruding portion 82 is slightly separated from the end portion 811 in the counter-clockwise direction. The protruding portion 82 includes a pair of protruding bodies 820 each having a plate shape. The pair of protruding bodies 820 protrude in the radial direction, centered on the center line C, from the outer side surface of the base portion 81. The pair of protruding bodies 820 have approximately the same shape, and are separated from each other in the extending direction. As shown in FIG. 6, of the pair of protruding bodies 820, end portions 821 on the side closer to the end portion 811 in the rotational direction extend in parallel to the radial direction, centered on the center line C. Of the pair of protruding bodies 820, end portions 822 on the side closer to the end portion 812 in the rotational direction are inclined with respect to the radial direction, centered on the center line C. At a position of the end portions 822, the height of the pair of protruding bodies 820 increases in the clockwise direction. A pair of protrusions 82P that protrude in the radial direction are provided at each of tip end portions 823, in the radial direction, of the pair of protruding bodies 820. The pair of protrusions 82P extend in the extending direction, and are separated from each other in the rotational direction.

As shown in FIG. 4, the protruding portion 83 is slightly separated from the end portion 812 in the clockwise direction. In a similar manner to the protruding portion 82, the protruding portion 83 includes a pair of protruding bodies 830 each having a plate shape. The pair of protruding bodies 830 protrude in the radial direction, centered on the center line C, from the outer side surface of the base portion 81. The pair of protruding bodies 830 have approximately the same shape, and are separated from each other in the extending direction. As shown in FIG. 6, of the pair of protruding bodies 830, end portions 832 on the side closer to the end portion 812 in the rotational direction extend in parallel to the radial direction, centered on the center line C. Of the pair of protruding bodies 830, end portions 831 on the side closer to the end portion 811 in the rotational direction are inclined with respect to the radial direction, centered on the center line C. At a position of the end portions 831, the height of the pair of protruding bodies 830 increases in the counter-clockwise direction. A pair of protrusions (not shown in the drawings) that have the same shape as the pair of protrusions 82P of the protruding portion 82 are provided at each of tip end portions of the pair of protruding bodies 830.

As shown in FIG. 4, the protruding portion 84 protrudes in the radial direction, centered on the center line C, at the end portion 812 of the base portion 81. The end portion 812 has a planar shape, and is orthogonal to the rotational direction. As shown in FIG. 6, of the protruding portion 84, an end portion 841 on the opposite side from the end portion 812 in the rotational direction is inclined with respect to the radial direction centered on the center line C. The length in the radial direction (the height) of the protruding portion 84 increases in the counter-clockwise direction at the position of the end portion 841. As shown in FIG. 4, a slit 813 that extends in the clockwise direction from the end portion 812 is provided at the base portion 81. Of the base portion 81, a portion further to the proximal end side than the slit 813 will be referred to as an elastic portion 810. The elastic portion 810 extends in the rotational direction. The elastic portion 810 can elastically deform in the radial direction centered on the center line C. The protruding portion 84 is formed at the distal end of the elastic portion 810.

As shown in FIG. 4, the base portion 86 curves so as to have a downward convex shape. End portions 861 and 862, and protruding portions 87, 88, and 89 of the base portion 86 respectively correspond to the end portions 811 and 812, and the protruding portions 82, 83, and 84 of the base portion 81. A pair of protruding bodies 870, an end portion 871, an end portion 872, and a pair of protrusions (not shown in the drawings) of the protruding portion 87 respectively correspond to the pair of protruding bodies 820, the end portion 821, the end portion 822, and the pair of protrusions 82P of the protruding portion 82. A pair of protruding bodies 880, an end portion 881, an end portion 882, and a pair of protrusions 88P of the protruding portion 88 respectively correspond to the pair of protruding bodies 830, the end portion 831, the end portion 832, and the pair of protrusions (not shown in the drawings) of the protruding portion 83. An end portion 891 of the protruding portion 89 corresponds to the end portion 841 of the protruding portion 84. A slit 863 and an elastic portion 860 of the base portion 86 respectively correspond to the slit 813 and the elastic portion 810 of the base portion 81.

Body 3

Figure 5:
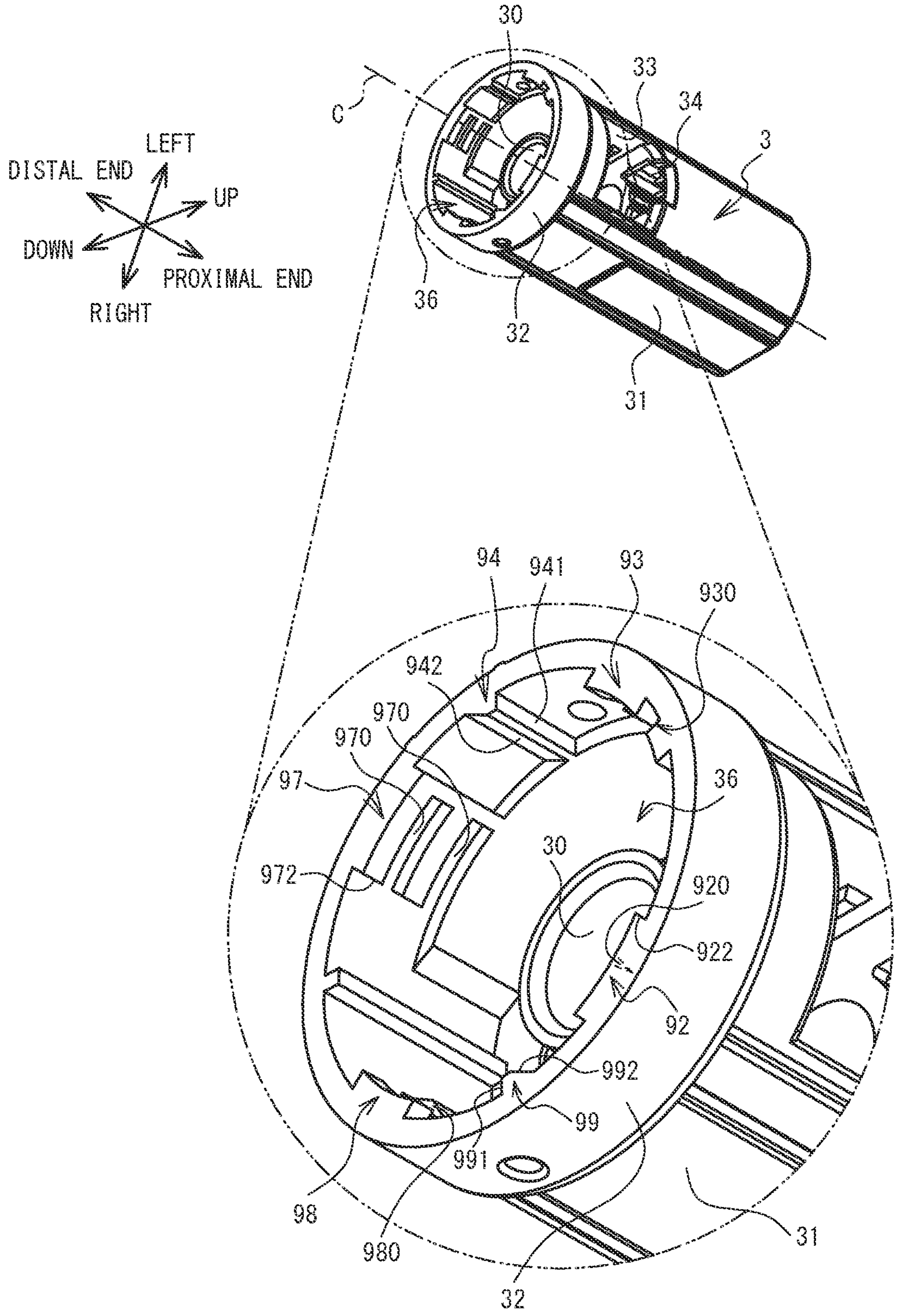
FIG. 5 is an expanded perspective view of a body.

As shown in FIG. 1 to FIG. 3, the body 3 is positioned to the proximal end side of the syringe 2, and includes a base portion 31, a flange 32, and a coupling portion 36 (refer to FIG. 2). The base portion 31 has a substantially circular cylindrical shape, and extends along the center line C. As shown in FIG. 5, a through hole 30 that extends along the center line C is formed in the base portion 31. The through hole 30 extends from the proximal end portion to the distal end portion of the base portion 31 and penetrates the base portion 31. The plunger 4 to be described later (refer to FIG. 3) is inserted into the through hole 30.

Figure 8:
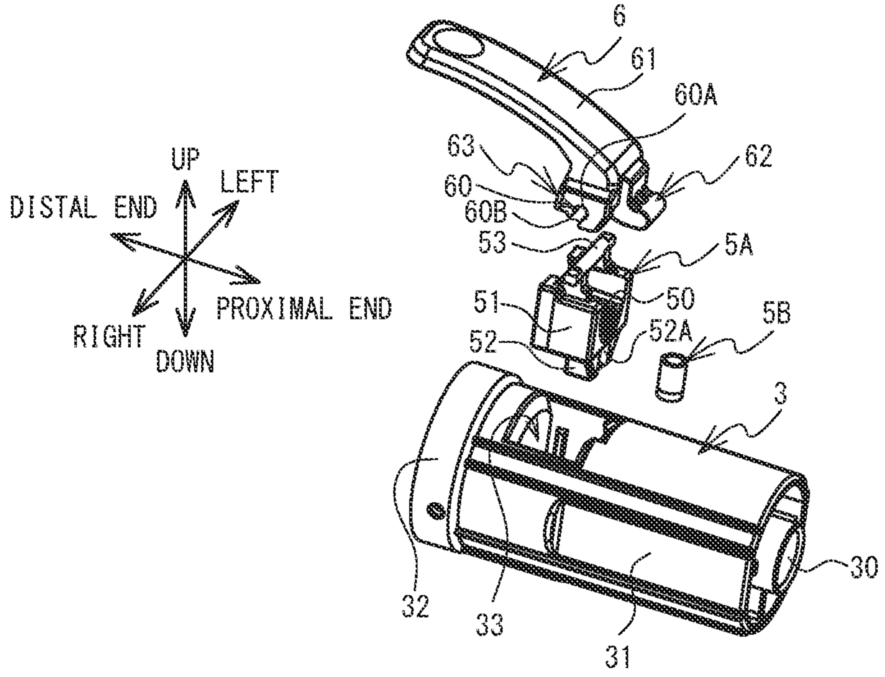
FIG. 8 is an exploded perspective view of the body, a regulating body, and a lever body.

A first hole portion 33, which is recessed downward, is formed in the vicinity of the distal end portion of the side surface of the base portion 31. An opening of the first hole portion 33 has a rectangular shape, and is formed at the upper end portion of the base portion 31. The first hole portion 33 is communicated with the through hole 30, and extends further downward than the through hole 30 (refer to FIG. 12 and FIG. 13). The bottom surface of the first hole portion 33 is positioned lower than the through hole 30. As shown in FIG. 8, the regulating body 5A, the urging member 5B, and a part of the lever body 6 to be described later are housed in the first hole portion 33. As shown In FIG. 5, a second hole portion 34, which is recessed toward the distal end side, is formed at a portion in the vicinity of the upper end of the inner side surface on the distal end side of the first hole portion 33. The second hole portion 34 extends toward the distal end side. A part of the lever body 6 (refer to FIG. 1 to FIG. 3) is housed in the second hole portion 34.

As shown in FIG. 1 to FIG. 3, the flange 32 is provided at the distal end portion of the base portion 31. As shown in FIG. 2, the flange 32 has a circular cylindrical shape, and the distal end portion thereof is open. The coupling portion 36 for coupling the body 3 and the syringe 2 is provided at the inner side surface of the flange 32.

Coupling Portion 36

As shown in FIG. 5, the coupling portion 36 includes engagement portions 92, 93, 94, 97, 98, and 99. The engagement portions 92, 93, 94, 97, 98, and 99 are provided at the inner side surface of the flange 32. The engagement portions 92, 93, 94, 97, 98, and 99 are aligned in this order in the counter-clockwise direction.

As shown in FIG. 5, each of the engagement portions 92, 93, 94, 97, and 98 protrudes to the inner side from the inner side surface of the flange 32. A pair of groove portions 970, which extend in the clockwise direction from an end portion 972 in the vicinity of the engagement portion 98, are provided in the engagement portion 97. The pair of groove portions 970 extend in parallel to each other while being separated in the extending direction. In a similar manner to the engagement portion 97, a pair of groove portions 920, which extend in the clockwise direction from an end portion 922 in the vicinity of the engagement portion 93, are provided in the engagement portion 92. The pair of groove portions 920 extend in parallel to each other while being separated in the extending direction. A pair of groove portions 930, which extend in the clockwise direction between both of end portions of the engagement portion 93, are provided in the engagement portion 93. The pair of groove portions 930 extend in parallel to each other while being separated in the extending direction. A pair of groove portions 980, which extend in the clockwise direction between both of end portions of the engagement portion 98, are provided in the engagement portion 98. The pair of groove portions 980 extend in parallel to each other while being separated in the extending direction.

The engagement portion 94 includes an end portion 941 in the vicinity of the engagement portion 93, and an end portion 942 in the vicinity of the engagement portion 97. The end portion 941 extends in the radial direction toward the center line C from the inner side surface of the flange 32. The end portion 941 has a planar shape, and is orthogonal to the rotational direction. The end portion 942 extends in a direction inclined with respect to the radial direction, toward the center line C from the inner side surface of the flange 32. At a position of the end portion 942, the height of the engagement portion 94 increases in the clockwise direction. The engagement portion 99 includes an end portion 991 in the vicinity of the engagement portion 98, and an end portion 992 in the vicinity of the engagement portion 92. The end portion 991 extends in the radial direction toward the center line C from the inner side surface of the flange 32. The end portion 992 extends in a direction inclined with respect to the radial direction, toward the center line C from the inner side surface of the flange 32. At a position of the end portion 992, the height of the engagement portion 99 increases in the clockwise direction.

Method of Coupling Syringe 2 and Body 3

The syringe 2 and the body 3 are coupled in an assembly processing of the pressurizing device 1. The syringe 2 and the body 3 are coupled by the coupling portion 26 and the coupling portion 36. A method of coupling the syringe 2 and the body 3 will be described below.

The syringe 2 and the body 3 are disposed in a state of being separated from each other in the extending direction. The syringe 2 is disposed at the distal end side and the body 3 is disposed at the proximal end side. Next, the syringe 2 and the body 3 are brought closer together. At this time, as shown in FIG. 6, the protruding portion 82 of the syringe 2 is inserted between the engagement portions 92 and 93 of the body 3. The protruding portion 83 of the syringe 2 is inserted between the engagement portions 93 and 94 of the body 3. The protruding portion 84 of the syringe 2 is inserted between the engagement portions 94 and 97 of the body 3. The protruding portion 87 of the syringe 2 is inserted between the engagement portions 97 and 98 of the body 3. The protruding portion 88 of the syringe 2 is inserted between the engagement portions 98 and 99. The protruding portion 89 of the syringe 2 is inserted between the engagement portions 99 and 92.

In this state, the syringe 2 is rotated in the clockwise direction with respect to the body 3. At this time, as shown in FIG. 7, the pair of protruding bodies 820 of the protruding portion 82 of the syringe 2 are inserted into the pair of groove portions 920 (refer to FIG. 5) of the engagement portion 92 of the body 3. The pair of protruding bodies 830 (refer to FIG. 4) of the protruding portion 83 of the syringe 2 are inserted into the pair of groove portions 930 (refer to FIG. 5) of the engagement portion 93 of the body 3. The pair of protruding bodies 870 of the protruding portion 87 of the syringe 2 are inserted into the pair of groove portions 970 (refer to FIG. 5) of the engagement portion 97 of the body 3. The pair of protruding bodies 880 (refer to FIG. 4) of the protruding portion 88 of the syringe 2 are inserted into the pair of groove portions 980 (refer to FIG. 5) of the engagement portion 98 of the body 3.

Further, the end portion 841 of the protruding portion 84 of the syringe 2 comes into contact with the end portion 942 of the engagement portion 94 of the body 3. The protruding portion 84 of the syringe 2 moves to the inner side as a result of the elastic portion 810 being elastically deformed, and passes over the engagement portion 94 of the body 3 in the clockwise direction. After the protruding portion 84 of the syringe 2 has passed over the engagement portion 94 of the body 3, the elastic portion 810 returns to an original state as a result of an elastic force. The end portion 812 of the syringe 2 comes into contact with the end portion 941 of the engagement portion 94 of the body 3. In a similar manner, the end portion 891 of the protruding portion 89 of the syringe 2 comes into contact with the end portion 992 of the engagement portion 99 of the body 3. The protruding portion 89 of the syringe 2 moves to the inner side as a result of the elastic portion 860 being elastically deformed, and passes over the engagement portion 99 of the body 3 in the clockwise direction. After the protruding portion 89 of the syringe 2 has passed over the engagement portion 99 of the body 3, the elastic portion 860 returns to an original state as a result of an elastic force. The end portion 862 of the syringe 2 comes into contact with the end portion 991 of the engagement portion 99 of the body 3. Here, the end portions 812 and 862 of the syringe 2, and the end portions 941 and 991 of the body 3 all extend in the radial direction centered on the center line C. Thus, in a state in which the end portion 812 of the syringe 2 is in contact with the end portion 941 of the body 3 and the end portion 862 of the syringe 2 is in contact with the end portion 991 of the body 3, the rotation of the syringe 2 in the counter-clockwise direction with respect to the body 3 is suppressed. In this way, the syringe 2 and the body 3 are coupled together and cannot be detached.

Regulating Body 5A, Urging Member 5B

Figure 9:
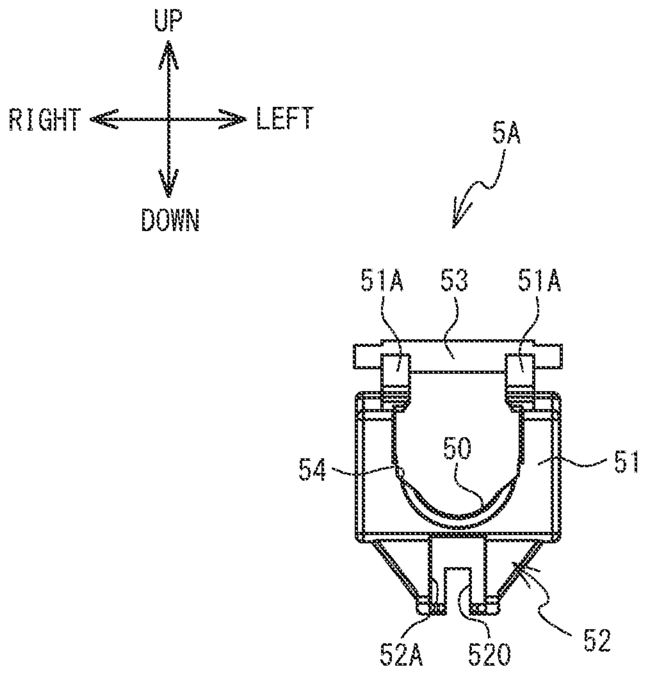
FIG. 9 is a view as seen from a proximal end side of the regulating body.
Figure 10:
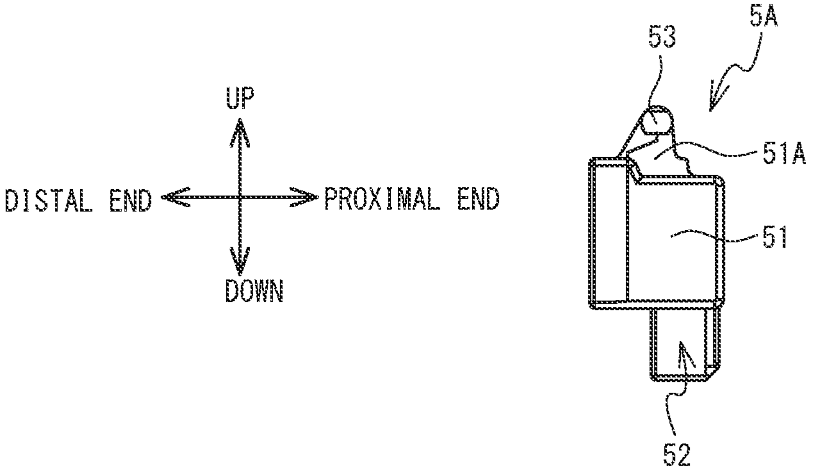
FIG. 10 is a right side view of the regulating body.

As shown in FIG. 3 and FIG. 8, in a state in which the regulating body 5A is housed inside the first hole portion 33 of the body 3, the regulating body 5A is supported by the body 3 by means of the first hole portion 33. The regulating body 5A can move in the up-down direction with respect to the body 3. As shown in FIG. 8, FIG. 9, and FIG. 10, the regulating body 5A includes a regulating member 51, a rib 52, and a rotation shaft 53. As shown in FIG. 9, the regulating member 51 is substantially U-shaped. The regulating member 51 includes a recessed portion 54 that is recessed downward from the upper end portion of the regulating member 51. The bottom portion of the recessed portion 54 is curved in an arc shape. A curvature of a bottom portion of the recessed portion 54 is equivalent to a curvature of the through hole 30 of the body 3 (refer to FIG. 8). In a state in which the regulating body 5A is housed in the first hole portion 33 of the body 3, a part of the recessed portion 54 of the regulating body 5A and the through hole 30 of the body 3 overlap in the extending direction (refer to FIG. 12 and FIG. 13). An internal helical gear 50 is formed in a curved portion of the bottom portion of the recessed portion 54.

The rib 52 protrudes downward from the lower end portion of the regulating member 51. A notch portion 520 that is cut out in the upward direction is provided in the lower end portion of the rib 52. A recessed portion 52A that is recessed toward the distal end side is formed in a surface on the proximal end side of the rib 52 (refer to FIG. 8). The upper end portion of the recessed portion 52A is covered by the lower end portion of the regulating member 51. The lower end portion of the recessed portion 52A is open. The rotation shaft 53 is coupled to the upper end portions of a pair of protruding portions 51A protruding upward from the upper end portion of the regulating member 51. The rotation shaft 53 has a circular cylindrical shape and extends between the pair of protruding portions 51A in the left-right direction. The left and right end portions of the rotation shaft 53 protrude further to the outside than the pair of protruding portions 51A.

Figure 12:
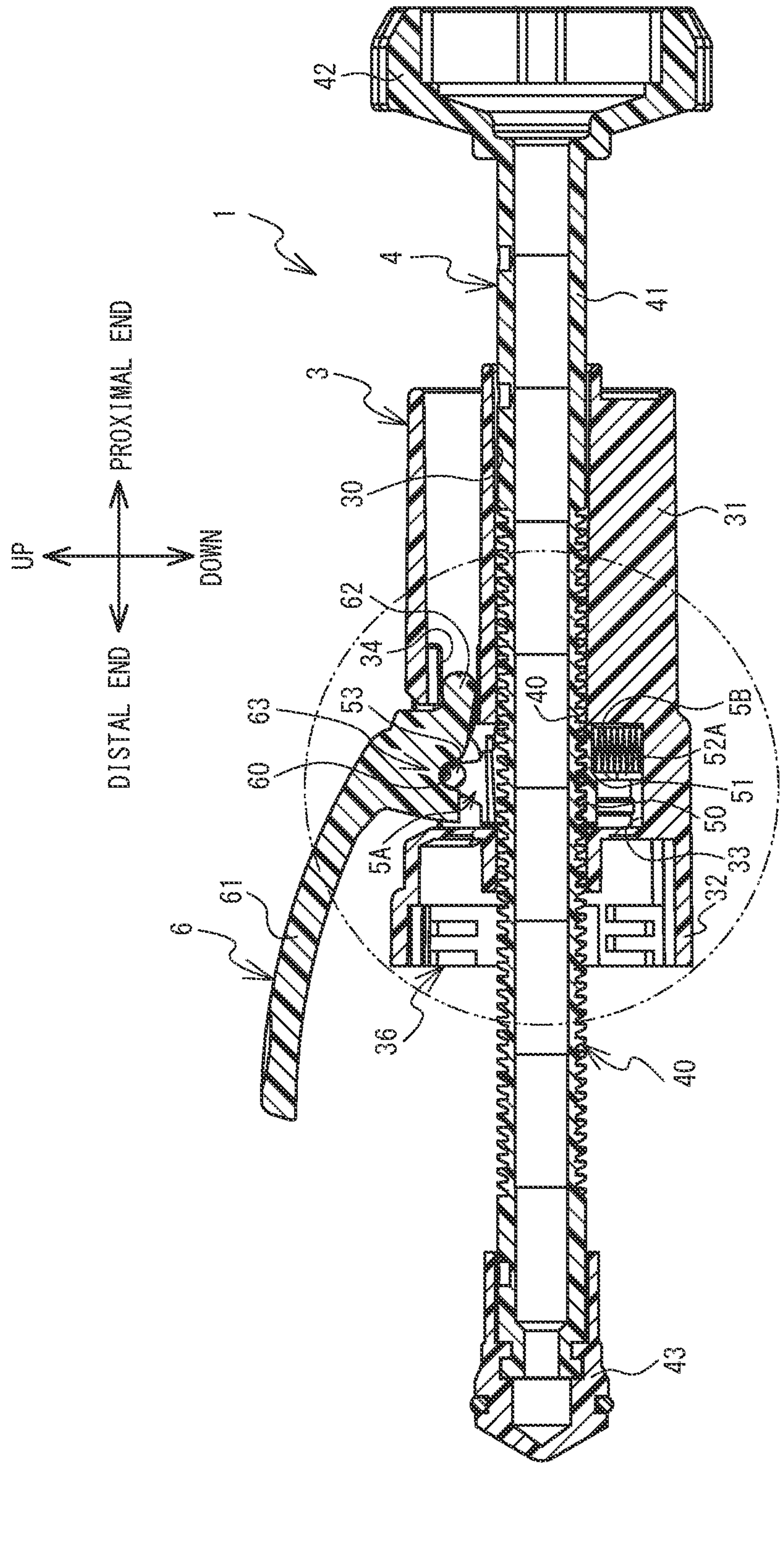
FIG. 12 is a cross-sectional view of the pressurizing device including the regulating body disposed at a contact position.
Figure 13:
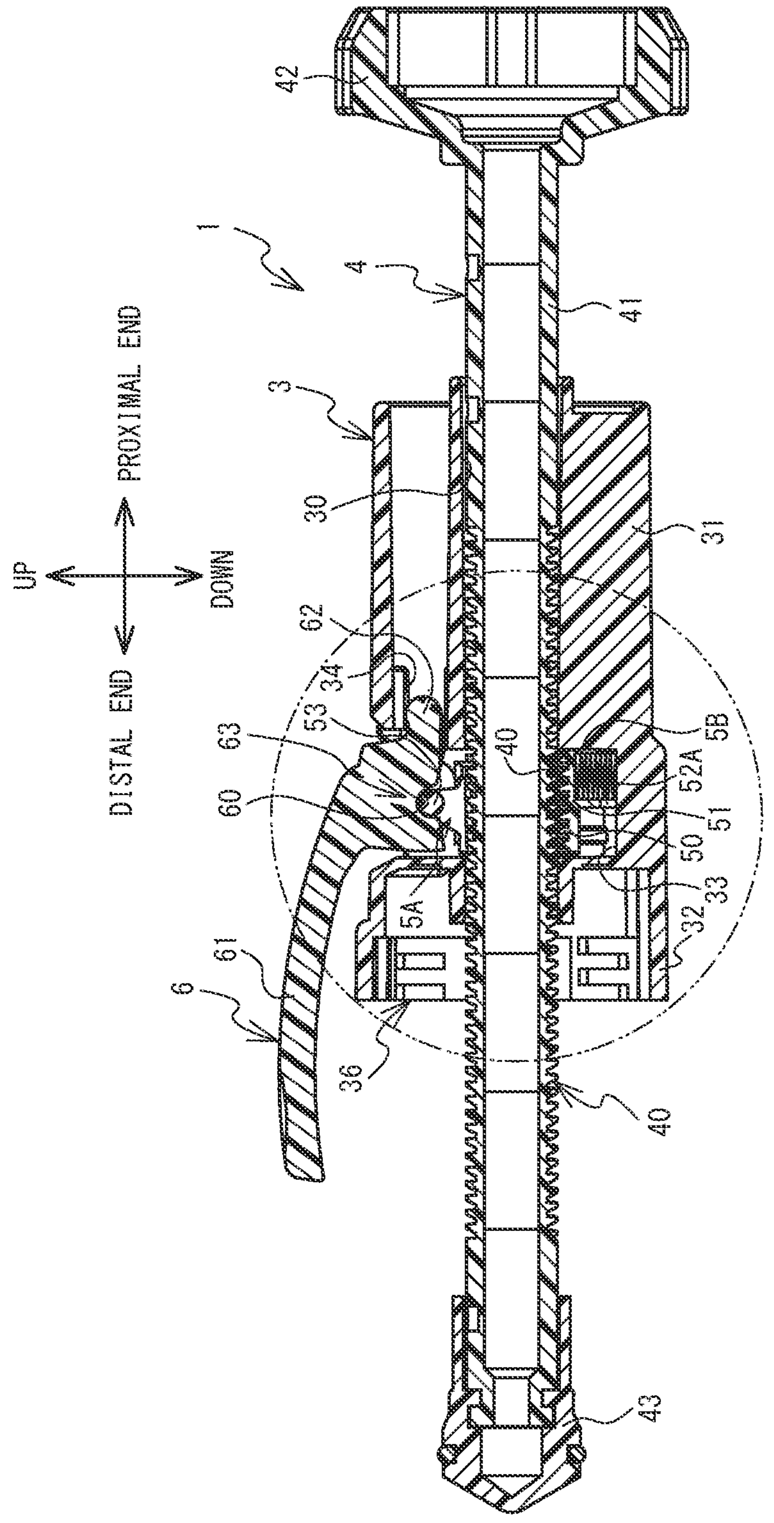
FIG. 13 is a cross-sectional view of the pressurizing device including the regulating body disposed at a separated position.

As shown in FIG. 8, the urging member 5B is a compression coil spring. The urging member 5B is housed in the recessed portion 52A formed in the rib 52 of the regulating body 5A, with an orientation of being able to extend and contract in the up-down direction. Positional displacement of the urging member 5B in the left-right direction is suppressed by the rib 52. As shown in FIG. 12 and FIG. 13, the upper end portion of the urging member 5B comes into contact, from below, with the regulating member 51 of the regulating body 5A. The lower end portion of the urging member 5B comes into contact, from above, with the bottom surface of the first hole portion 33 of the body 3. The urging member 5B urges the regulating body 5A upward.

Lever Body 6

Figure 11:
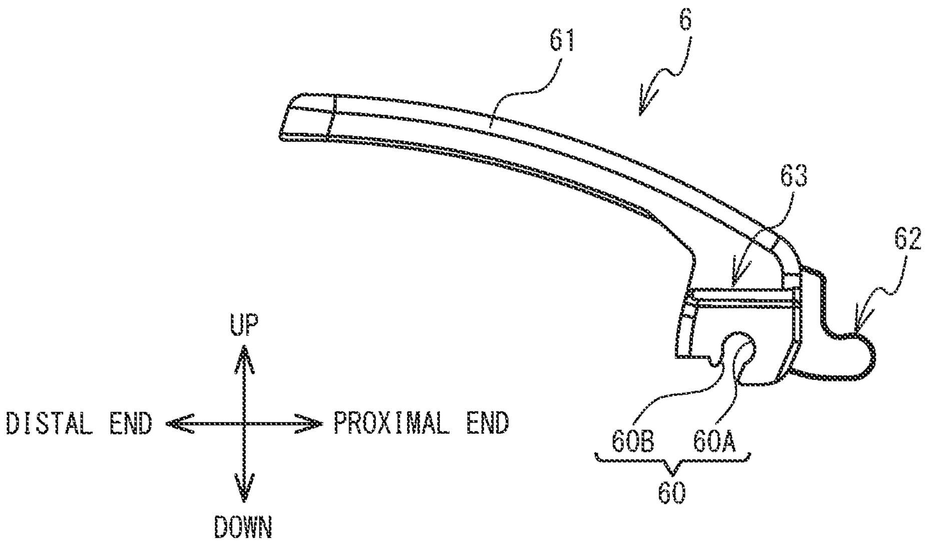
FIG. 11 is a right side view of the lever body.

As shown in FIG. 1 and FIG. 2, the lever body 6 is rotatably supported in the vicinity of the distal end portion of the base portion 31, of the upper end portion of the body 3. As shown in FIG. 8 and FIG. 11, the lever body 6 includes a lever 61, a protruding portion 62, and a support portion 63. The support portion 63 is positioned between the lever 61 and the protruding portion 62. The support portion 63 includes a through hole 60A that penetrates between both side surfaces on the left and right sides of the support portion 63, and a communication portion 60B that extends downward from the through hole 60A. The through hole 60A and the communication portion 60B are integrally formed and form a groove portion 60 in the bottom surface of the support portion 63. The protruding portion 62 protrudes from the side surface on the proximal end side of the support portion 63 toward the proximal end side. A corner at a tip end portion of the protruding portion 62 is curved. The lever 61 has a plate shape that is long and thin, and curved. The lever 61 extends to the distal end side from the upper side surface of the support portion 63, while being inclined upward.

As shown in FIG. 12 and FIG. 13, the support portion 63 of the lever body 6 is rotatably supported by the rotation shaft 53, as a result of the rotation shaft 53 of the regulating body 5A being fitted into the groove portion 60. Respective positions of the regulating body 5A, the rotation shaft 53, and the support portion 63 overlap with each other in the up-down direction. The lever 61 is rotatably supported on the regulating body 5A by the support portion 63. A center of rotation of the lever body 6 is aligned with the rotation shaft 53 disposed in the through hole 60A of the groove portion 60. Note that the position of the rotation shaft 53 moves in accordance with the regulating body 5A moving in the up-down direction inside the first hole portion 33. In other words, the center of rotation of the lever body 6 moves in the up-down direction in accordance with the movement of the regulating body 5A. The movement direction of the center of rotation of the lever body 6 is aligned with the direction in which the regulating body 5A can move. The protruding portion 62 of the lever body 6 is inserted, from the tip end portion, into the second hole portion 34 of the body 3. The position of the tip end of the protruding portion 62 can move in the extending direction in accordance with the rotation of the lever body 6.

Plunger 4

As shown in FIG. 3, the plunger 4 includes a rod 41, a knob 42, and a gasket 43. The rod 41 has a circular cylindrical shape and extends in the extending direction along the center line C. The diameter of the rod 41 is substantially the same as the diameter of the through hole 30 (refer to FIG. 8) of the body 3. The curvature of the rod 41 is the same as the curvature of the bottom portion of the recessed portion 54 of the regulating body 5A. A helical gear 40 is formed at the peripheral surface of the rod 41.

The knob 42 is provided at the proximal end portion of the rod 41. As shown in FIG. 1 and FIG. 2, the knob 42 has a plate shape and is orthogonal to the extending direction. The end portion of the knob 42 is curved in a wave shape. The knob 42 is gripped when a user performs an operation to rotate the plunger 4. As shown in FIG. 2 and FIG. 3, the gasket 43 is provided at the distal end portion of the rod 41. The gasket 43 is made of rubber, and has a larger diameter than the diameter of the rod 41. The gasket 43 is provided in order to enhance a closeness of fit with the storage portion 20 of the syringe 2.

The plunger 4 is supported at the body 3 in a state in which the rod 41 is inserted into the through hole 30 of the body 3. The rod 41 passes, in the extending direction, through the inside of the recessed portion 54 of the regulating member 51 that is housed in the first hole portion 33 of the body 3. The knob 42 is positioned further to the proximal end side than the body 3. The gasket 43 is positioned further to the distal end side than the body 3, and is positioned inside the storage portion 20 of the syringe 2. The plunger 4 can move in the extending direction with respect to the syringe 2, the body 3, and the regulating body 5A. When the plunger 4 moves to the distal end side, the fluid housed in the storage portion 20 is discharged to the outside via the connection port 23 of the syringe 2.

Movement of Regulating Member 51 Due to Operation of Lever 61

The regulating member 51 receives the upward urging force from the urging member 5B. As shown in FIG. 12, when an external force is not acting on the lever 61 of the lever body 6, the regulating member 51 moves upward in accordance with the urging force received from the urging member 5B. At this time, the bottom portion of the recessed portion 54 of the regulating member 51 comes into contact, from the lower side, with a part of the rod 41 of the plunger 4. A part of the helical gear 40 of the rod 41 meshes with the internal helical gear 50. The urging member 5B extends. Hereinafter, the position of the regulating member 51 in the state in which the bottom portion of the recessed portion 54 is in contact with the part of the rod 41 of the plunger 4 (the position shown in FIG. 12) will be referred to as a contact position.

When a downward external force acts on the lever 61 of the lever body 6, the lever body 6 rotates around the rotation shaft 53 in the counter-clockwise direction as seen from the right side. As shown in FIG. 13, the protruding portion 62 of the lever body 6 rotates around the rotation shaft 53 and moves upward inside the second hole portion 34 of the body 3. The upward movement of the protruding portion 62 is regulated by the protruding portion 62 coming into contact, from the lower side, with the upper side of the inner side surface of the second hole portion 34. At this time, the lever body 6 forms a second class lever in which the lever 61 acts as a point of application, the support portion 63 acts as a point of action, and the protruding portion 62 acts as a point of support. Thus, the downward force acting on the lever 61 acts on the support portion 63, and causes the support portion 63 and the rotation shaft 53 to move downward. In this way, the regulating member 51 receives the downward force in resistance to the urging force of the urging member 5B. The regulating member 51 moves downward from the contact position.

Note that the protruding portion 62 of the lever body 6 is not fixed to the body 3, and thus, when the lever 61 rotates, the protruding portion 62 moves slightly to the proximal end side along the second hole portion 34. However, the positions of the rotation shaft 53 of the regulating body 5A, and the support portion 63 supported by the rotation shaft 53 do not move in the extending direction, and only move in the up-down direction. Thus, a force transmitted to the regulating member 51 from the lever 61 via the support portion 63 and the rotation shaft 53 acts in a directly downward direction, and does not act in a direction inclined with respect to the downward direction.

In accordance with the regulating member 51 moving downward, the bottom portion of the recessed portion 54 of the regulating member 51 is separated, downward, from the part of the rod 41 of the plunger 4. The state in which the part of the helical gear 40 of the rod 41 is meshed with the internal helical gear 50 is released. The urging member 5B contracts. Hereinafter, a position of the regulating member 51 in the state in which the bottom portion of the recessed portion 54 is separated from the part of the rod 41 of the plunger 4 (a position shown in FIG. 13) will be referred to as a separated position.

Method of Use

The user connects the end portion on the proximal end side of the catheter, which is provided with the balloon on the distal end portion thereof, to the connection port 23 of the syringe 2. The fluid for inflating the balloon is stored in advance in the storage portion 20 of the cylindrical body 21 of the syringe 2. In the state in which the external force is not acting on the lever 61, the regulating member 51 moves upward in accordance with the urging force of the urging member 5B, and is positioned at the contact position. The internal helical gear 50 of the regulating member 51 meshes with the part of the helical gear 40 of the rod 41 of the plunger 4. Thus, the movement in the extending direction of the plunger 4 is regulated by the regulating member 51.

The user holds and rotates the knob 42 of the plunger 4. Since the rod 41 rotates in the state in which the internal helical gear 50 of the regulating member 51 is meshed with the part of the helical gear 40, the rod 41 moves to the distal end side. The gasket 43 of the plunger 4 presses the fluid stored in the storage portion 20 of the syringe 2 to the outside, via the connection port 23. The fluid pressed out from the syringe 2 flows into the balloon via the catheter. In this way, the balloon inflates, and treats an affected part. By adjusting a rotation amount of the knob 42 of the plunger 4, the user can control the pressure of the fluid flowing into the balloon.

Note that, in accordance with the pressure of the fluid increasing as a result of the plunger 4 moving to the distal end side, a force toward the proximal end side acts on the plunger 4. However, the regulating member 51 is at the contact position, and the internal helical gear 50 of the regulating member 51 is meshed with the part of the helical gear 40 of the rod 41 of the plunger 4. Thus, the movement to the proximal end side of the plunger 4 is regulated by the regulating member 51.

After treating the affected part using the inflation of the balloon, the user grips the lever 61 and causes the downward external force to act on the lever 61. The lever body 6 rotates around the rotation shaft 53, and moves the support portion 63 and the rotation shaft 53 downward. The regulating member 51 receives the downward force in resistance to the urging force of the urging member 5B, and moves from the contact position to the separated position. The state in which the part of the helical gear 40 of the rod 41 of the plunger 4 is meshed with the internal helical gear 50 is released. The plunger 4 receives the pressure of the fluid inside the storage portion 20 of the syringe 2, and moves to the proximal end side. The pressure of the fluid decreases, and the fluid is discharged from the balloon. In this way, the balloon rapidly deflates.

Operations and Effects of the Present Embodiment

When the lever body 6 is operated by the user and rotated, the lever 61 can apply a downward force to the regulating member 51, and cause the regulating member 51 to move from the contact position to the separated position. Here, the protruding portion 62 of the lever body 6 is not fixed to the body 3. Further, the support portion 63 of the lever body 6, the regulating member 51 of the regulating body 5A, and the rotation shaft 53 are disposed so as to overlap with each other in the up-down direction. Thus, the lever 61 can apply the downward force to the regulating member 51 without changing the position of the rotation shaft 53 in the extending direction. In this case, compared to a case in which the force applied to the regulating member 51 by the lever 61 is dispersed in directions other than the downward direction, an operation force of the lever 61 required in order to move the regulating member 51 from the contact position to the separated position is small. Thus, the pressurizing device 1 can improve the operability for the user.

When the knob 42 of the plunger 4 is rotated, and the fluid is caused to be discharged from the syringe 2 to the balloon, and the balloon is inflated, the pressure of the fluid increases. Due to this pressure, a force in the direction toward the proximal end side acts on the plunger 4. Thus, a part of the helical gear 40 of the rod 41 of the plunger 4 is strongly pressed against the internal helical gear 50 of the regulating member 51 at the contact position. As a result, the regulating member 51 is in a state in which it is difficult to move from the contact position toward the separated position. In contrast to this, by the user operating the lever 61 in this state, and moving the regulating member 51 from the contact position to the separated position, the plunger 4 can move to the proximal end side. At this time, the lever body 6 can efficiently transfer the downward force on the lever 61 to the regulating member 51. Thus, the user can suppress a force required for operating the lever 61. As a result, the user can easily perform an operation, with respect to the lever 61, to switch from the state in which the movement of the plunger 4 to the proximal end side is regulated to the state in which the plunger 4 can move to the proximal end side in the pressurizing device 1.

In the pressurizing device 1, the rotation shaft 53 is provided at the regulating member 51 and the support portion 63 is provided at the lever 61. In this case, compared to a case in which the regulating member 51 and the rotation shaft 53 are separately provided, and the lever 61 and the support portion 63 are separately provided, the pressurizing device 1 can increase the rigidity of the rotation shaft 53 and the support portion 63. Thus, the pressurizing device 1 can move the regulating member 51, in accordance with the operation by the user on the lever 61, in a stable manner.

The pressurizing device 1 is provided with the urging member 5B that urges the regulating member 51 upward from the separated position to the contact position. The urging member 5B can dispose the regulating member 51 at the contact position in a stable manner, in a state in which the operation is not performed on the lever 61.

The urging member 5B can hold the regulating member 51 at the contact position in a stable manner. Thus, the pressurizing device 1 can stably maintain the state in which the regulating member 51 disposed at the contact position regulates the movement of the plunger 4 to the proximal end side. Thus, the user can easily maintain the state in which the balloon is inflated by the fluid discharged from the storage portion 20 of the syringe 2 by the movement to the distal end side of the plunger 4.

The urging member 5B is the compression coil spring. The urging member 5B contracts when the regulating member 51 is at the separated position, and urges the regulating member 51 toward the contact position. On the other hand, the urging member 5B extends when the regulating member 51 is at the contact position. The pressurizing device 1 can easily realize the urging member, using the spring, for holding the regulating member 51 at the contact position.

The rib 52 for inhibiting positional displacement of the urging member 5B is provided at the regulating member 51. In this case, the pressurizing device 1 can urge the regulating member 51 in a stable manner using the urging member 5B, and can thus dispose the regulating member 51 at the contact position in a stable manner.

The plunger 4 includes the helical gear 40, and the regulating member 51 includes the internal helical gear 50. In this case, the regulating member 51 can appropriately suppress the movement of the plunger 4 to the proximal end side, in the state in which the regulating member 51 is disposed at the contact position. Further, the user can move the plunger 4 to the distal end side by rotating the plunger 4 in the state in which the regulating member 51 is disposed at the contact position.

The body 3 of the pressurizing device 1 supports the regulating body 5A such that the regulating body 5A can move in the up-down direction. In this case, the body 3 can stabilize the position of the regulating member 51 of the regulating body 5A in the extending direction, and can appropriately regulate the movement of the plunger 4 using the regulating member 51. Further, the regulating body 5A moves between the contact position and the separated position by moving in the up-down direction along the first hole portion 33 of the body 3. In this case, the pressurizing device 1 can suppress rattling of the regulating body 5A in the extending direction with respect to the body 3, and can thus efficiently transmit the force acting on the lever 61 to the regulating body 5A.

The lever body 6 forms the second class lever in which the lever 61 acts as the point of application, the protruding portion 62 acts as the point of support, and the support portion 63 acts as the point of action. Further, when the lever body 6 rotates, the protruding portion 62 moves slightly to the proximal end side along the second hole portion 34 of the body 3. On the other hand, the rotation shaft 53 of the regulating body 5A and the support portion 63 of the lever body 6 do not move in the extending direction. In this case, the lever body 6 can efficiently transmit the force in the up-down direction acting on the lever 61 to the regulating member 51, and can move the regulating member 51 in the up-down direction.

The coupling portion 26 of the syringe 2 includes the protruding portion 84 provided at the elastic portion 810, and the protruding portion 89 provided at the elastic portion 860. The coupling portion 36 of the body 3 includes the engagement portions 94 and 99. The protruding portion 84 moves to the inner side as a result of the elastic portion 810 elastically deforming, and passes over the engagement portion 94 in the clockwise direction. After that, as a result of the elastic portion 810 returning to its original state due to the elastic force, the end portion 812 of the protruding portion 84 comes into contact with the end portion 941 of the engagement portion 94. Further, the protruding portion 89 moves to the inner side as a result of the elastic portion 860 elastically deforming, and passes over the engagement portion 99 in the clockwise direction. After that, as a result of the elastic portion 860 returning to its original state due to the elastic force, the end portion 862 of the protruding portion 89 comes into contact with the end portion 991 of the engagement portion 99. Thus, the pressurizing device 1 can couple the syringe 2 and the body 3 with a firm connection, using the coupling portions 26 and 36, without using an adhesive or the like, and a possibility can thus be reduced of the adhesive or the like becoming mixed with the fluid inside the syringe 2.

When the operation to press the fluid stored in the storage portion 20 to the outside of the syringe 2 is performed, a force acts on the syringe 2 and the body 3 in a direction to cause the syringe 2 and the body 3 to separate from each other along the extending direction. In contrast to this, a direction of relative movement of the syringe 2 and the body 3 with respect to each other in a process to couple the syringe 2 and the body 3 (the rotational direction around the center line C), is orthogonal to the extending direction that is an arrangement direction of the syringe 2 and the body 3. Thus, even if a force repeatedly acts on the syringe 2 and the body 3 in a direction to cause the syringe 2 and the body 3 to separate from each other, the pressurizing device 1 can effectively suppress the syringe 2 and the body 3 from becoming detached from each other. As a result, the pressurizing device 1 can maintain a state in which the syringe 2 and the body 3 are firmly coupled to each other for a long period of time.

The end portions 812 and 862 of the protruding portions 84 and 89, and the end portions 941 and 991 of the body 3 all have the planar shape, and extend in the radial direction centered on the center line C. Thus, in the state in which the end portion 812 of the syringe 2 and the end portion 941 of the body 3 are in contact with each other, and the end portion 862 of the syringe 2 and the end portion 991 of the body 3 are in contact with each other, the rotation of the syringe 2 in the counter-clockwise direction with respect to the body 3 is suppressed. The end portions 812 and 862 of the protruding portions 84 and 89, and the end portions 941 and 991 of the body 3 are in contact with each other over a planar-shaped wide area, and the rotation of the body 3 with respect to the syringe 2 can be regulated. Thus, the pressurizing device 1 can stably maintain the state in which the syringe 2 and the body 3 are coupled together, and can suppress the occurrence of dimensional errors in each unit.

Each of the protruding portions 82, 83, 87, and 88 of the coupling portion 26 includes the pair of protrusions 82P, 88P and the like, which protrude in the radial direction, at the tip end portions 823, 883, and the like in the radial direction. In the state in which the protruding portions 82, 83, 87, and 88 are inserted into the groove portions 920, 930, 970, and 980 of the body 3, the pairs of protrusions 82P, 88P, and the like come into contact with the bottom portions of the groove portions 920, 930, 970, and 980. Even if slight irregularities are formed on the bottom portions of the groove portions 920, 930,970, and 980, and on the tip end portions 823, 883, and the like of the protruding portions 82, 83, 87, and 88, the pair of protrusions 82P, 88P, and the like can stabilize the positions in the radial direction of the protruding portions 82, 83, 87, and 88 inside the groove portions 920, 930, 970, and 980. Thus, using the pair of protrusions 82P and 88P, the pressurizing device 1 can resolve the dimensional errors of the syringe 2 and the body 3.

While the invention has been described in conjunction with various example structures outlined above and illustrated in the figures, various alternatives, modifications, variations, improvements, and/or substantial equivalents, whether known or that may be presently unforeseen, may become apparent to those having at least ordinary skill in the art. Accordingly, the example embodiments of the disclosure, as set forth above, are intended to be illustrative of the invention, and not limiting the invention. Various changes may be made without departing from the spirit and scope of the disclosure. Therefore, the disclosure is intended to embrace all known or later developed alternatives, modifications, variations, improvements, and/or substantial equivalents. Some specific examples of potential alternatives, modifications, or variations in the described invention are provided below:

MODIFIED EXAMPLES

The present disclosure is not limited to the above-described embodiment, and various modifications are possible. The syringe 2 and the body 3 may be inseparable. In other words, the syringe 2 and the body 3 may be integrally provided.

The rotation shaft 53 may be included in the lever body 6 instead of the regulating body 5A. For example, the rotation shaft 53 may be provided at the lever 61. The support portion 63 may be included in the regulating body 5A instead of the lever body 6. A rotation mechanism of the rotation shaft 53 and the support portion 63 may be provided separately from the regulating body 5A and the lever body 6.

A lock mechanism maybe provided that holds the regulating member 51 at each of the contact position and the separated position. For example, the lock mechanism may hold the position of the lever 61 in states in which the regulating member 51 is positioned at the contact position and the separated position, respectively. In this case, the pressurizing device 1 need not necessarily include the urging member 5B.

The urging member 5B is not limited to being the compression coil spring and may be another member having elasticity. For example, the urging member 5B may be a rubber piece or the like. The rib 52 may be provided at the bottom surface of the first hole portion 33 of the body 3. The rib 52 may be formed in a rod shape passing through the center of the compression coil spring that is the urging member 5B.

The plunger 4 and the regulating member 51 need not necessarily include gears. For example, the regulating member 51 may regulate the movement of the plunger 4 to the proximal end side using a frictional force occurring in accordance with contact with the rod 41 of the plunger 4 in the state in which the regulating member 51 is at the contact position.

What is claimed is:

1. A pressurizing device comprising:

a syringe internally including a storage portion configured to store a fluid;

a plunger configured to move in a first direction with respect to the syringe, and discharging the fluid stored in the storage portion to outside of the syringe when the plunger moves to one side in the first direction;

a body connected to the syringe and internally including a through hole through which the plunger is inserted;

a regulating member configured to move in a second direction intersecting the first direction, between a separated position of being separated from the plunger and a contact position of being in contact with the plunger;

a lever configured to rotate about a rotation axis to move the regulating member from the contact position to the separated position in accordance with a rotation operation; and a rotation mechanism including the rotation axis and provided at a position overlapping with the regulating member in the second direction, supporting the lever to be rotatable with respect to the regulating member, configured to move in the second direction in accordance with rotation of the lever, and configured to move, when moving to one side in the second direction, the regulating member from the contact position to the separated position by applying a force to the regulating member, wherein the body includes a first hole portion communicated with the through hole, and a second hole portion extending along the first direction from a side surface of the first hole portion, the regulating member is supported by the body and is configured to move between the contact position of being in contact with the plunger inserted through the through hole and the separated position by moving along the first hole portion, the pressurizing device further includes a lever body including the lever, a protruding portion provided at one end of the lever and housed in the second hole portion, and a part of the rotation mechanism positioned between the lever and the protruding portion, when the lever rotates, the protruding portion moves in the first direction along the second hole portion and the rotation mechanism does not move in the first direction, and wherein the lever serves as a point of force application, the protruding portion serves as a point of support, and the part of the rotation mechanism serves as a point of action.

2. The pressurizing device according to claim 1, wherein:

the rotation mechanism includes a rotation shaft provided on one of the lever and the regulating member, and a support portion provided on the other of the lever and the regulating member, and rotatably supported by the rotation shaft.

3. The pressurizing device according to claim 1, further comprising:

an urging member configured to urge the regulating member along the second direction from the separated position toward the contact position.

4. The pressurizing device according to claim 3, wherein:

the urging member is a spring; and the spring contracts when the regulating member is at the separated position and urges the regulating member toward the contact position, and extends when the regulating member is at the contact position.

5. The pressurizing device according to claim 3, wherein:

an inhibition mechanism configured to inhibit positional displacement of the urging member is provided at the regulating member.

6. The pressurizing device according to claim 1, wherein:

the plunger includes a gear; and the regulating member includes an internal gear meshing with the gear when the regulating member is disposed at the contact position.

7. The pressurizing device according to claim 6, wherein:

the gear of the plunger is a helical gear; and the internal gear of the regulating member is an internal helical gear.

* * * * *